(12) United States Patent
Dehesh

(10) Patent No.: US 6,706,950 B2
(45) Date of Patent: Mar. 16, 2004

(54) NUCLEIC ACID SEQUENCES ENCODING β-KETOACYL-ACP SYNTHASE AND USES THEREOF

(75) Inventor: Katayoon Dehesh, Vacaville, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/915,182

(22) Filed: Jul. 25, 2001

(65) Prior Publication Data

US 2002/0059661 A1 May 16, 2002

Related U.S. Application Data

(60) Provisional application No. 60/220,702, filed on Jul. 25, 2000.

(51) Int. Cl.$^7$ ............... C12N 15/31; C12N 15/82; A01H 5/00; A01H 5/10; C12P 7/64

(52) U.S. Cl. ............... 800/281; 800/278; 800/286; 800/306; 800/312; 800/320.1; 800/288; 435/419; 536/23.7; 536/24.5

(58) Field of Search ............... 800/278, 281, 800/286, 288, 306, 312, 320.1; 435/419; 536/23.7, 24.5

(56) References Cited

U.S. PATENT DOCUMENTS

| | | | |
|---|---|---|---|
| 5,378,619 A | 1/1995 | Rogers | |
| 5,500,361 A | 3/1996 | Kinney | |
| 5,510,255 A | * 4/1996 | Knauf | 435/172.3 |
| 5,585,535 A | 12/1996 | Fehr et al. | |
| 5,693,507 A | 12/1997 | Daniell et al. | |
| 5,723,595 A | 3/1998 | Thompson et al. | |
| 5,952,544 A | 9/1999 | Browse et al. | |
| 6,200,788 B1 | 3/2001 | Ferri et al. | |
| 6,222,099 B1 | 4/2001 | Gengenbach et al. | |

FOREIGN PATENT DOCUMENTS

| | | | |
|---|---|---|---|
| EP | 0120 515 | 3/1984 | |
| EP | 0 969 014 | 1/2000 | |
| WO | 92/03564 | 3/1992 | |
| WO | 93/10240 | 5/1993 | |
| WO | 94/10189 | 5/1994 | |
| WO | WO 97/10328 | 3/1997 | |
| WO | WO-98/32770 | * 7/1998 | C12N/9/00 |
| WO | WO 98/46776 | 10/1998 | |
| WO | 00/07433 | 2/2000 | |
| WO | 00/75343 | 12/2000 | |
| WO | 01/29238 | 4/2001 | |

OTHER PUBLICATIONS

Fourgoux–Nicol et al, 1999, Plant Molecular Biology 40 : 857–872.*
Broun et al. Science vol. 282, Nov. 13, 1998 pp. 1315–1317.*
Dehesh K. et al., Plant Physiology, Feb. 2001, vol. 125, pp. 1103–1114.*
Kaneko T. et al., GenBank Accession No. S77464, DNA Research, vol. 3, pp. 109–136, Jun. 19, 1996.*
International Search Report of PCT/US01/23369 dated Sep. 25, 2002 (4 pages).
Dehesh et al., Database EMBL, Accession No. AX073486 (Jan. 24, 2001) (XP002213168).
Kaneko et al., Database EMBL, Accession No. D90905 (Oct. 31, 1996) (XP002213167).
Kaneko et al., "Sequence Analysis of the Genome of the Unicellular Cyanobacterium *Synechocytis* sp. Strain PCC6803. II. Sequence Determination of the Entire Genome and Assignment of Potential Protein–coding Regions", *DNA Research*, vol. 3, pp. 109–136 (1996).
Leonard et al., "A *Cuphea* β–ketoacyl–ACP synthase shifts the synthesis of fatty acids towards shorter chains in *Arabidopsis* seeds expressing *Cuphea* FatB thioesterases", *The Plant Journal*, 13(5), pp. 621–628 (1998).
Ohlrogge, "Design of New Plant Products: Engineering of Fatty Acid Metabolism", *Plant Physiol.*, vol. 104, pp. 821–826 (1994).
Knowles, P.F. (1988) Recent advances in oil crops breeding. In World Conference on Biotechnology for the Fats and Oils Industry: Proceedings (Applewhite, T.E., ed.). American Oil Chemists' Society, pp. 35–38.
Siggaard–Andersen, M., Wissenbach, M., Chuck, J.A., Svendsen, I., Olsen, J.G. and von Wettstein–knowles, P. (1994) The fabJ–encoded beta–ketoacyl–[acyl carrier protein] synthase IV from *Escherichia coli* is sensitive to cerulenin and specific for short–chain substrates. *Proc. Natl. Acad. Sci. USA*. 91: 11027–11031.
Dehesh, K., Edwards, P., Fillatti, J., Slabaugh, M. and Byrne, J. (1998) KAS IV: a 3–ketoacyl–ACP synthase from *Cuphea sp.* is a medium chain specific condensing enzyme. *Plant J.* 15(3):383–390.
Gould, S.J., Subramani, S. and Scheffler, I.E. (1989) Use of the DNA polymerase chain reaction for homology probing: isolation of partial cDNA or genomic clones encoding the iron–sulfur protein of succinate dehydrogenase from several species. *Proc. Natl. Acad. Sci. USA* 86: 1934–1938.

(List continued on next page.)

Primary Examiner—David T. Fox
Assistant Examiner—Russell Kallis
(74) *Attorney, Agent, or Firm*—Thomas P. McBride; Arnold & Porter

(57) ABSTRACT

This invention relates to sequences encoding β–ketoacyl–ACP synthase (KAS) and methods of use thereof. Also provided are methods for decreasing saturated fatty acid levels as a component of total triglycerides found in plant oils. The method generally comprises growing a soybean plant having integrated into its genome a DNA construct comprising, in the 5' to 3' direction of transcription, a promoter functional in a soybean plant seed cell, a DNA sequence encoding a KAS protein, and a transcription termination region functional in a plant cell. The present invention also provides a soybean seed with less than about 3.5 weight percent total saturated fatty acids.

20 Claims, 6 Drawing Sheets

OTHER PUBLICATIONS

Jaworski, J.G., Clough, R.C. and Barnum, S.R. (1989) A cerulenin insensitive short chain 3–ketoacyl–acyl carrier protein synthase in *Spinacia oleracea* leaves. *Plant Physiol.* 90: 41–44.

Clough, R.C., Matthis, A.L., Barnum, S.R. and Jaworski, J.G. (1992) Purification and characterization of 3–ketoacyl–acyl carrier protein synthase III from spinach: a condensing enzyme utilizing acetyl–coenzyme A to initiate fatty acid synthesis. *J. Biol. Chem.* 267(29):20992–20998.

Jaworski, J.G., Post–Beittenmiller, D. and Ohlrogge, J.B. (1993) Acetyl–acyl carrier protein is not a major intermediate in fatty acid biosynthesis in spinach. *Eur. J. Biochem.* 213(3): 981–987.

Shimakata, T. and Stumpf, P.K. (1982) Fatty acid synthetase of *Spinacia oleracea* leaves. *Plant Physiol.* 69: 1257–1262.

Shimakata, T. and Stumpf, P.K. (1982) Isolation and function of spinach leaf beta–ketoacyl–[acyl carrier protein] synthases. *Proc. Natl. Acad. Sci. USA* 79:5808–5812.

Kauppinen, S., Siggaard–Andersen, M. and von Wettstein–Knowles, P. (1988) Beta–ketoacyl–ACP synthase I of *Escherichia coli*: nucleotide sequence of the fabB gene and identification of the cerulenin binding residue. *Carlsberg Res. Commun.* 53: 357–370.

Coulson, A. (1994) High–performance searching of biosequence databases. *Trends in Biotech.* 12: 76–80.

Baxevanis, A.D., Boguski, M.S. and Ouellette B.F.F. (1997) Computational analysis of DNA and protein sequences. In Genome Analysis: a laboratory manual, vol. 1: Analyzing DNA (Birren, B., Green, E.D., Klapholz, S., Myers, R.M. and Roshams, J., eds.) 1: 543–559.

Magnuson, K., Carey, M.R. and Cronan, J.E., Jr. (1995) The putative fabJ gene of *Escherichia coli* fatty acid synthesis is the fabF gene. *J. Bacteriol.* 177(12): 3593–3595.

Edwards, P., Nelsen, J.S., Metz, J.G. and Dehesh, K. (1997) Cloning of the fabF gene in an expression vector an in vitro characterization of recombinant fabF and fabB encoded enzymes from *Escherichia coli*. *FEBS Letters* 402: 62–66.

Garwin, J.L., Klages, A.L. and Cronan, J.E., Jr. (1980) Beta–ketoacyl–acyl carrier protein synthase II of *Escherichia coli*: evidence for function in the thermal regulation of fatty acid synthesis. *J. Biol. Chem.* 255(8): 3263–3265.

Moche, M., Dehesh, K., Edwards, P. and Lindqvist, Y. (2001) The crystal structure of beta–ketoacyl–acyl carrier protein synthase II from *Synechocystis sp.* at 1.54 Å resolution and its relationship to other condensing enzymes. *J. Mol. Biol.* 305: 491–503.

Chen. Z.–L., Schuler, M.A. and Beachy, R.N. (1986) Functional analysis of regulatory elements in a plant embryo–specific gene. *Proc. Natl. Acad. Sci. USA* 83: 8560–8564.

Thompson, G.A., Scherer, D.E., Foxall–Van Aken, S., Kenny, J.W., Young, H.L., Shintani, D.K., Kridl, J.C. and Knauf, V.C (1991) Primary structures of the precursor and mature forms of stearoyl–acyl carrier protein desaturase from safflower embryos and requirement of ferredoxin for enzyme activity. *Proc. Natl. Acad. Sci. USA* 88: 2578–2582.

Wu, J., Lightner, J., Warwick, N. and Browse, J. (1997) Low–temperature damage and subsequent recovery of fab1 mutant Arabidopsis exposed to 2'C. *Plant Physiol.* 113(2): 347–356.

\* cited by examiner

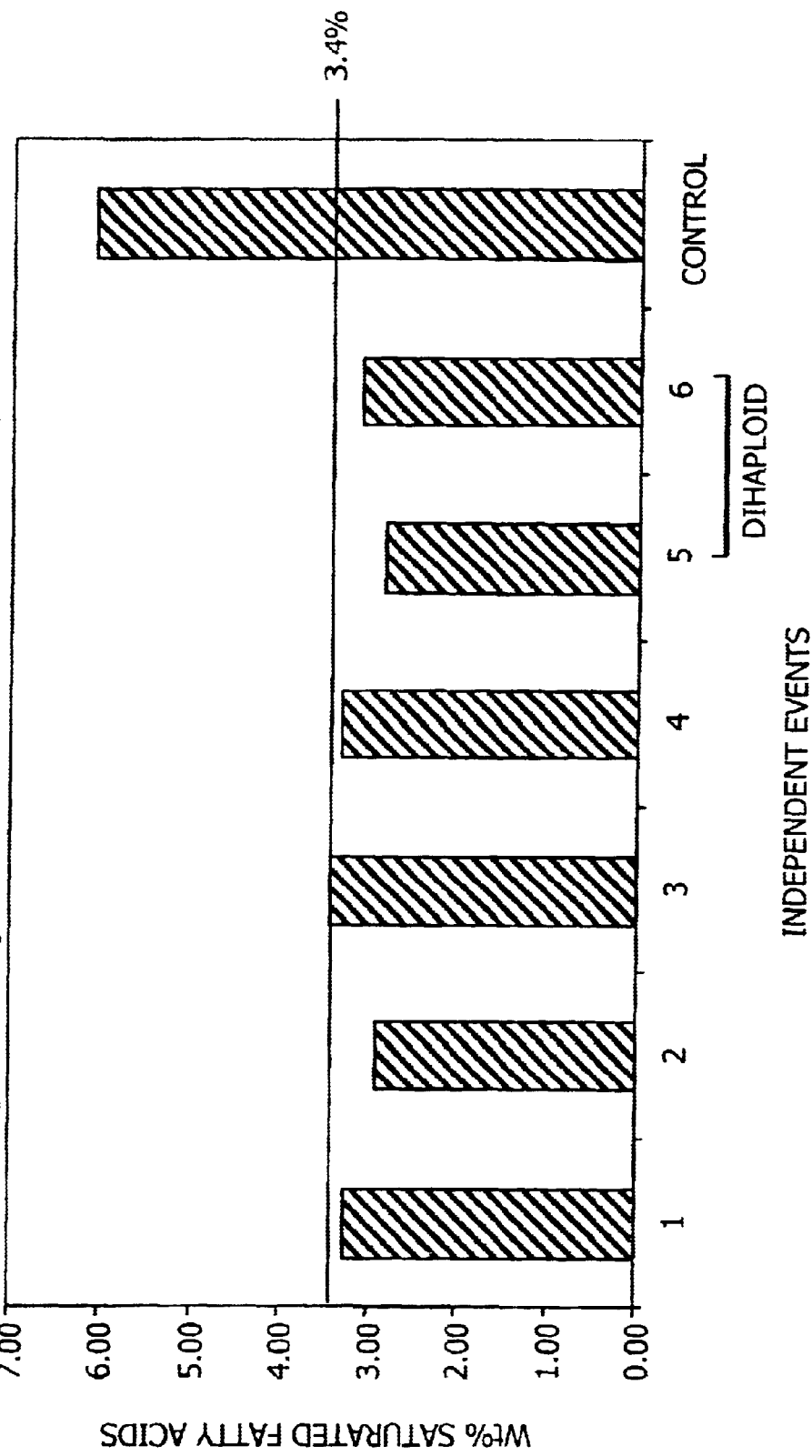

FIG. 2A

| SAMPLE ID | 12:0 | 14:0 | 16:0 | 18:0 | 22:0 | total sat | 16:1 | 18:1 | 18:2 | 18:3 | 20:0 | 20:1 | 20:2 |
|---|---|---|---|---|---|---|---|---|---|---|---|---|---|
| GM_A5187 | 0 | 0.04 | 2.46 | 4.91 | 0.4 | 7.81 | 0.03 | 31.32 | 50.56 | 6.08 | 0.44 | 3.12 | 0.38 |
| GM_A4747 | 0 | 0.04 | 3.37 | 4.14 | 0.32 | 7.87 | 0.07 | 43.59 | 37.44 | 6.7 | 0.39 | 3.55 | 0.29 |
| GM_A6260 | 0 | 0.05 | 3.37 | 6.55 | 0.39 | 10.36 | 0.06 | 20 | 56.68 | 8.76 | 0.5 | 2.88 | 0.58 |
| GM_A6168 | 0 | 0.03 | 3.95 | 4.78 | 0.34 | 9.1 | 0.04 | 31.27 | 49.85 | 7.34 | 0.38 | 1.72 | 0.27 |
| GM_A5467 | 0.03 | 0.15 | 5.91 | 5.56 | 0.36 | 12.01 | 0.03 | 21.83 | 55.24 | 8.5 | 0.46 | 1.63 | 0.3 |
| GM_A5551 | 0.03 | 0.09 | 5.92 | 5.24 | 0.37 | 11.65 | 0.15 | 22.51 | 53.66 | 9.49 | 0.5 | 1.72 | 0.26 |
| GM_A6669 | 0 | 0.62 | 6.81 | 4.38 | 0.37 | 12.18 | 0.04 | 21.4 | 56.37 | 8.58 | 0.36 | 0.82 | 0.22 |
| GM_A5525 | 0 | 0.06 | 6.89 | 4.39 | 0.38 | 11.72 | 0.05 | 26.1 | 50.36 | 8.28 | 0.37 | 2.53 | 0.36 |
| GM_A6262 | 0 | 0.09 | 7.02 | 5.27 | 0.45 | 12.83 | 0.06 | 22.07 | 51.96 | 10.08 | 0.55 | 1.97 | 0.46 |
| GM_A6491 | 0.02 | 0.42 | 7.24 | 3.91 | 0.34 | 11.93 | 0.05 | 20.12 | 58.84 | 7.93 | 0.31 | 0.67 | 0.14 |
| GM_A5181 | 0 | 0.08 | 7.83 | 4.43 | 0.3 | 12.64 | 0.14 | 24.19 | 52.77 | 8.13 | 0.36 | 1.44 | 0.31 |
| GM_A6259 | 0 | 0.18 | 7.87 | 4.92 | 0.42 | 13.39 | 0.05 | 24.66 | 52.25 | 8.38 | 0.39 | 0.72 | 0.12 |
| GM_A5177 | 0.01 | 0.3 | 8.22 | 4.01 | 0.37 | 12.91 | 0.07 | 35.21 | 44.47 | 6.26 | 0.36 | 0.64 | 0.06 |
| GM_A5549 | 0.01 | 0.1 | 8.54 | 4.73 | 0.35 | 13.73 | 0.07 | 20.48 | 54.41 | 9.43 | 0.38 | 1.21 | 0.27 |
| GM_A5519 | 0 | 0.07 | 8.84 | 3.82 | 0.35 | 13.08 | 0.08 | 28.38 | 49.02 | 7.92 | 0.34 | 1.04 | 0.11 |

CONTINUED TO FIG. 2B

FIG. 2B CONTINUED FROM FIG. 2A

| | | | | | | | | | | | | | |
|---|---|---|---|---|---|---|---|---|---|---|---|---|---|
| GM_A7153 | 0 | 0 | 8.87 | 3.94 | 0.4 | 13.21 | 0.09 | 29.81 | 47.71 | 7.27 | 0.34 | 1.3 | 0.2 |
| GM_A6695 | 0 | 0.59 | 9.18 | 5.1 | 0.42 | 15.29 | 0.09 | 16.44 | 55.76 | 10.73 | 0.4 | 0.96 | 0.34 |
| GM_A5176 | 0 | 0.04 | 9.63 | 3.84 | 0.4 | 13.91 | 0.1 | 35.37 | 41.94 | 6.54 | 0.46 | 1.22 | 0.14 |
| GM_A5492 | 0.01 | 0.41 | 9.64 | 4.97 | 0.43 | 15.46 | 0.1 | 16.58 | 58.19 | 8.78 | 0.41 | 0.36 | 0.07 |
| GM_A5472 | 0 | 0.2 | 9.82 | 3.83 | 0.41 | 14.26 | 0.08 | 24.18 | 53.14 | 7.47 | 0.37 | 0.38 | 0.1 |
| GM_A4745 | 0 | 0.09 | 10.23 | 3.97 | 0.39 | 14.68 | 0.13 | 23.12 | 54.32 | 7.01 | 0.33 | 0.32 | 0.05 |
| GM_A5191 | 0.01 | 0.11 | 10.51 | 3.71 | 0.4 | 14.74 | 0.09 | 30.1 | 48.47 | 5.51 | 0.35 | 0.44 | 0.08 |
| GM_A6481 | 0 | 0.34 | 10.55 | 3.82 | 0.5 | 15.21 | 0.09 | 30.42 | 46.78 | 6.35 | 0.37 | 0.37 | 0.04 |
| GM_A5477 | 0 | 0.14 | 10.56 | 4.41 | 0.43 | 15.54 | 0.08 | 23.44 | 53.31 | 6.82 | 0.38 | 0.32 | 0.09 |
| GM_A5495 | 0 | 0.32 | 10.66 | 3.72 | 0.41 | 15.11 | 0.09 | 22.32 | 53.89 | 7.8 | 0.33 | 0.29 | 0.12 |
| GM_A5196 | 0 | 0.29 | 10.73 | 4.18 | 0.42 | 15.62 | 0.09 | 21.27 | 54.9 | 7.45 | 0.34 | 0.28 | 0.05 |
| GM_A6177 | 0.01 | 0.11 | 10.77 | 4 | 0.45 | 15.34 | 0.13 | 27.4 | 50.41 | 5.99 | 0.38 | 0.34 | 0.06 |
| GM_A6171 | 0 | 0.68 | 11.01 | 4.87 | 0.47 | 17.03 | 0.08 | 20.34 | 53.11 | 8.54 | 0.4 | 0.32 | 0.06 |
| GM_A6680 | 0 | 0.33 | 11.08 | 4.22 | 0.44 | 16.07 | 0.09 | 22.97 | 53.11 | 6.96 | 0.42 | 0.32 | 0.07 |
| GM_A5478 | 0.02 | 0.32 | 11.09 | 4.25 | 0.45 | 16.13 | 0.13 | 18.52 | 56.79 | 7.71 | 0.37 | 0.3 | 0.09 |
| GM_A6181 | 0 | 0.36 | 11.12 | 4.92 | 0.46 | 16.86 | 0.09 | 19.17 | 54.49 | 8.51 | 0.42 | 0.31 | 0.1 |
| GM_A6178 | 0.02 | 0.12 | 11.16 | 4.77 | 0.43 | 16.5 | 0.09 | 20.09 | 54.05 | 8.06 | 0.39 | 0.31 | 0.05 |
| GM_A5178 | 0 | 0 | 11.18 | 3.91 | 0.33 | 15.42 | 0.25 | 29.66 | 44.58 | 8.68 | 0.35 | 0.9 | 0.16 |

CONTINUED FROM FIG. 2B

| SPL ID | 12:0 | 14:0 | 16:0 | 18:0 | 22:0 | total sat | 16:1 | 18:1 | 18:2 | 18:3 | 20:0 | 20:1 | 20:2 |
|---|---|---|---|---|---|---|---|---|---|---|---|---|---|
| GM_A5186 | 0 | 0.12 | 11.25 | 4.46 | 0.47 | 16.3 | 0.09 | 29.62 | 46.03 | 7.09 | 0.41 | 0.37 | 0.05 |
| GM_A6186 | 0.02 | 0.12 | 11.29 | 5.02 | 0.46 | 16.91 | 0.08 | 18.21 | 55.02 | 9.02 | 0.41 | 0.27 | 0.08 |
| GM_A7154 | 0 | 0.33 | 11.29 | 4.48 | 0.43 | 16.53 | 0.13 | 21.15 | 52.75 | 8.65 | 0.39 | 0.33 | 0.08 |
| GM_A6496 | 0.02 | 0.34 | 11.43 | 4.26 | 0.39 | 16.44 | 0.09 | 17.45 | 57.22 | 8.09 | 0.37 | 0.28 | 0.06 |
| GM_A5840 | 0 | 0.17 | 11.47 | 4.45 | 0.42 | 16.51 | 0.09 | 19.45 | 55.16 | 8.01 | 0.4 | 0.31 | 0.07 |
| GM_A5489 | 0 | 0.12 | 11.56 | 4.18 | 0.44 | 16.3 | 0.09 | 20.87 | 53.25 | 8.67 | 0.38 | 0.31 | 0.09 |
| GM_A6183 | 0 | 0.54 | 12.04 | 5.41 | 0.48 | 18.47 | 0.09 | 18.49 | 52.39 | 9.59 | 0.54 | 0.3 | 0.12 |
| GM_A6174 | 0 | 0.12 | 12.1 | 5.07 | 0.47 | 17.76 | 0.1 | 25.09 | 48.44 | 7.8 | 0.42 | 0.31 | 0.04 |
| GM_A6492 | 0 | 0.52 | 12.17 | 4.82 | 0.44 | 17.95 | 0.08 | 20.23 | 52.06 | 8.77 | 0.44 | 0.31 | 0.15 |
| GM_A5524 | 0 | 0.12 | 12.25 | 5.31 | 0.48 | 18.16 | 0.09 | 20.79 | 50.95 | 9.23 | 0.45 | 0.29 | 0.05 |
| GM_A5554 | 0.02 | 0.38 | 12.51 | 4.54 | 0.43 | 17.88 | 0.14 | 14.5 | 56.25 | 10.48 | 0.39 | 0.26 | 0.09 |
| GM_A6689 | 0 | 0 | 12.82 | 5.28 | 0.53 | 18.63 | 0.14 | 19.71 | 51.13 | 9.59 | 0.46 | 0.26 | 0.08 |
| GM_A6180 | 0 | 0.5 | 13.02 | 4.98 | 0.44 | 18.94 | 0.06 | 17.21 | 53.43 | 9.63 | 0.4 | 0.25 | 0.07 |

NUCLEIC ACID SEQUENCES ENCODING β-KETOACYL-ACP SYNTHASE AND USES THEREOF

CROSS-REFERENCE TO RELATED APPLICATIONS

This application claims the priority of U.S. Provisional Application Ser. No. 60/220,702, filed Jul. 25, 2000, herein incorporated by reference in its entirety.

TECHNICAL FIELD

The present invention is directed in general to β-ketoacyl-ACP synthase nucleic acid and amino acid sequences and constructs, and methods related thereto.

BACKGROUND OF THE INVENTION

Plant lipids have become indispensable in a number of industrial and nutritional applications. More importantly, plant lipids are used extensively for their nutritional value, which is determined by a plant's fatty acid composition. The value of any plant lipid is determined by its chemical structure, which is a result of a plant's metabolic processes. The chemical structure is characterized by varied degrees of unsaturation. Most vegetable oils from commercial plant varieties are composed primarily of palmitic (16:0), stearic (18:0), oleic (18:1), linoleic (18:2) and linolenic acid (18:3) acids.

Numerous research efforts have shown lipids to play a major role in development of many diseases, especially cardiovascular disorders. Recent research has examined in great detail the role of saturated and unsaturated fatty acids in potentiating the risk of coronary heart disease. Previously, it was believed that mono-unsaturated fatty acids had no effect on serum cholesterol and coronary heart disease risk. On the other hand, saturated fatty acids were considered to contribute to coronary heart disease while poly-unsaturated fatty acids were supposed to lower the risk of the same. It is now known that intake of both mono-unsaturated and poly-unsaturated fatty acids is beneficial for the heart and overall health. Several recent human clinical studies suggest that diets high in mono-unsaturated and/or poly-unsaturated fat and low in saturated fat may reduce the "bad" (low-density lipoprotein or LDL) cholesterol while maintaining the "good" (high-density lipoprotein or HDL) cholesterol. For example, a study performed by Mensink et al. concluded that a diet rich in mono-unsaturated fatty acids was as effective as a diet rich in (n-6)poly-unsaturated fats in lowering "bad" cholesterol (Mensink et al., N Engl J Med 321(7)436–441, August 1989). Furthermore, another study found that a diet rich in poly-unsaturated fats has a similar effect on "good" cholesterol concentrations in the blood as a diet rich in mono-unsaturated fats (Dreon et al., JAMA 263(18):2462–2466, May 9, 1990). Animal studies have also shown that when monkeys are fed mono-unsaturated and poly-unsaturated fat diets, they have similar concentrations of LDL cholesterol, and these values are significantly lower than the LDL values from animals that are fed saturated fats (Rudel et al., Arteriosclerosis, Thrombosis, and Vascular Biology, 15:2101–2110, 1995).

Therefore, a vegetable oil low in total saturates and high in mono-unsaturates and/or poly-unsaturates would provide significant health benefits to all consumers. The beneficial effects of oils high in poly-unsaturated fatty acids extend beyond lowering LDL cholesterol. For instance, linoleate and linolenate are essential fatty acids in human diets, rendering any edible oil high in these fats a useful nutritional supplement. Certain plants naturally possess high levels of poly-unsaturated fatty acids. This is exemplified by linseed oil, which is derived from the Flax plant (*Linum usitatissimum*) and contains over 50% linolenic acid. The oil content of flax is comparable to canola (around 40% dry weight of seed), however, high yields are only obtained in warm temperatures or subtropical climates. In addition, flax is highly susceptible to rust infection in the U.S. Therefore, even though natural plant sources of high poly-unsaturates exist, they are not always useful for large scale oil production. It would be commercially useful if a common crop such as canola, soybean or corn could be genetically transformed in such a way to minimize saturated fatty acid content.

To this effect, mutation-breeding programs have shown some promise in altering the levels of poly-unsaturated fatty acid levels in the edible oils of agronomic species. Examples of commercially grown varieties are high (85%) oleic sunflower and low (2%) linolenic flax (Knowles, (1980) pp. 35–38 in Applewhite, T. E., Ed., World Conference on Biotechnology for the Fats and Oils Industry Proceedings, American Oil Chemists' Society). However, these breeding programs are difficult to maintain and yields are often low. Hence, the option of production of transgenic plants is a desirable alternative for altering the content of saturated fats.

The enzymes of the fatty acid biosynthetic pathways are useful in creating transgenic plants that have altered fatty acid content. The β-ketoacyl-ACP (acyl carrier protein) family of synthase enzymes (also referred to herein as KAS) is especially attractive for plant transformation due to their indispensable role in fatty acid synthesis. To summarize their functions briefly, KAS III catalyzes the condensation of acetyl-CoA and malonyl-ACP to yield acetoacetyl-ACP in the first elongating reaction, KAS I utilizes saturated $C_2$–$C_{14}$ and unsaturated $C_{16:1}$–$C_{18:1}$ acyl-ACPs as substrates for condensation with a $C_2$ unit derived from malonyl-ACP; KAS II carries out the final extension step of unsaturated fatty acid biosynthesis ($C_{16:1}$ to $C_{18:1}$) by utilizing $C_{14:0}$ and $C_{12:1}$–$C_{16:1}$ acyl-ACPs. KAS IV has a substrate specificity between those of KAS III and KAS I, and is a medium chain specific condensing enzyme. See Siggaard-Andersen et al., *Proc. Natl. Acad. Sci.*, Vol. 91, pp. 11027–11031, November 1994, and Dehesh et al., *Plant J*, 15(3):383–390, August 1998.

To elaborate, the biosynthesis of fatty acids is a complex process, involving numerous enzymes and multiple plant compartments. The production of fatty acids in plants begins in the plastid with the reaction between acetyl-CoA and malonyl-ACP to produce butyryl-ACP. Elongation of acetyl-ACP to 16- and 18-carbon fatty acids involves the cyclical action of the following sequence of reactions: condensation with a two-carbon unit from malonyl-ACP, reduction of the keto-function to an alcohol, dehydration to form an enoyl-ACP, and finally reduction of the enoyl-ACP to form the elongated saturated acyl-ACP. KAS I, catalyzes elongation up to palmitoyl-ACP ($C_{16:0}$), whereas KAS II catalyzes the final elongation to stearoyl-ACP ($C_{18:0}$). The longest chain fatty acids produced by the fatty acid synthases are typically 18 carbons long. A further fatty acid biochemical step occurring in the plastid is the desaturation of stearoyl-ACP ($C_{18:0}$) to form oleoyl-ACP ($C_{18:1}$) in a reaction catalyzed by a delta-9 desaturase.

Once the $C_{18:1}$-ACP has been formed, the products undergo de-esterification, which allows movement into the cytoplasm, wherein they are incorporated into the "eukaryotic" lipid biosynthesis pathway. This occurs in the endoplasmic reticulum, which is responsible for the formation of phospholipids, triglycerides and other neutral lipids. Following transport of fatty acyl CoA's to the endoplasmic reticulum, subsequent sequential steps for triglyceride production can take place. For example, polyunsaturated fatty acyl groups such as linoleoyl and a-linolenoyl, are produced as the result of sequential desaturation of oleoyl acyl groups by the action of membrane-bound enzymes. Triglycerides are formed by action of the 1-, 2-, and 3-acyl-ACP transferase enzymes glycerol-3-phosphate acyltransferase, lysophosphatidic acid acyltransferase and diacylglycerol acyltransferase. Alternatively, fatty acids are linked to glycerol-3-phosphate (prokaryotic path), further unsaturated, and used for synthesis of chloroplast lipids. A portion of cytoplasmic lipids returns to the chloroplast. The preferential use of either eukaryotic or prokaryotic pathway depends on the particular plant species. The fatty acid composition of a plant cell is a reflection of the free fatty acid pool and the fatty acids (fatty acyl groups) incorporated into triglycerides as a result of the acyltransferase activities.

The properties of a given triglyceride will depend upon the various combinations of fatty acyl groups in the different positions in the triglyceride molecule. In general, vegetable oils tend to be mixtures of different triglycerides. The triglyceride oil properties are therefore a result of the combination of triglycerides which make up the oil, which are in turn influenced by their respective fatty acyl compositions.

There have been attempts to generate transgenic plants that would exhibit altered fatty acid levels for purposes of providing better nutritional value and herbicide and/or cold resistance. For instance, transformation of plants with maize acetyl CoA carboxylase or delta-15 desaturase can alter the fatty acid content in the plants. See U.S. Pat. Nos. 6,222,099 and 5,952,544 respectively. Transformation of plants with maize acetyl CoA carboxylase gene allows for altering the total oil content in the plant. However, this process does not provide a method for specifically increasing only the levels of unsaturated fats, which would in turn decrease the levels of saturated fats in the transgenic plants. U.S. Pat. No. 5,500,361 describes a nucleotide sequence that encodes for a β-ketoacyl-ACP synthase II enzyme. However, the disclosed compositions are limited in their use. Similarly, U.S. Pat. No. 6,200,788, also discloses a nucleotide sequence that encodes for a specific β-ketoacyl-ACP synthase II enzyme and has the same limitations.

Depending upon the intended oil use, various different oil compositions are desired. For example, edible oil sources containing the minimum possible amounts of saturated fatty acids are desired for dietary reasons and alternatives to current sources of highly saturated oil products, such as tropical oils, are also needed. Furthermore, oils compositions containing rare or exotic fatty acid species having nutritional benefits are also needed in the art. To this end, therefore, novel vegetable oils compositions and/or improved means to obtain or manipulate fatty acid compositions, from biosynthetic or natural plant sources, are needed.

Accordingly, a need still exists to produce transgenic plants that would possess lower levels of saturated fats compared to the levels in untransformed plants. These transgenic plants would provide a valuable nutritional supplement, especially if the oils extracted from them were incorporated into diets of people who were at risk for or suffered from cardiovascular diseases. Thus a need exists for a multi-functional KAS synthase that can effectively alter the saturated fatty acid content of a commercial plant. Thus, the identification of nucleic acid sequences encoding enzymes capable of producing altered saturated fatty acid compositions in host cells is needed in the art. Ultimately, useful nucleic acid constructs having the necessary elements to provide a phenotypic modification and host cells containing such constructs are needed.

SUMMARY OF THE INVENTION

The present invention is directed to fatty acid synthase, and in particular to β-ketoacyl-ACP synthase (also referred to herein as KAS) polypeptides and polynucleotides. In one aspect of the present invention, the polypeptides and polynucleotides are derived from cyanobacterial sources.

In another aspect of the invention polynucleotides encoding novel polypeptides, particularly, polynucleotides that encode β-ketoacyl-ACP synthase, are provided.

In a further aspect the invention relates to oligonucleotides derived from the β-ketoacyl-ACP synthase proteins and oligonucleotides which include partial or complete β-ketoacyl-ACP synthase encoding sequences.

It is also an aspect of the present invention to provide recombinant DNA constructs which can be used for transcription or transcription and translation (expression) of β-ketoacyl-ACP synthase. In particular, constructs are provided which are capable of transcription or transcription and translation in host cells. Particularly preferred constructs are those capable of transcription or transcription and translation in host plant cells.

In another aspect of the present invention, methods are provided for production of β-ketoacyl-ACP synthase in a host cell or progeny thereof. In particular, host cells are transformed or transfected with a DNA construct which can be used for transcription or transcription and translation of β-ketoacyl-ACP synthase. The recombinant cells which contain β-ketoacyl-ACP synthase are also part of the present invention.

In a further aspect, the present invention relates to methods of using polynucleotide and polypeptide sequences to modify the fatty acid composition in a host cell, particularly the fatty acid composition in the seed tissue of host plants. In particular, host plants such as Brassica, corn and soybean. And in further aspect of the invention, the modified fatty acid composition comprises an altered amount of saturated fatty acids. Plant cells having such a modified fatty acids are also contemplated herein.

The modified plants, seeds, their progeny and oils obtained by the expression of the plant β-ketoacyl-ACP synthase proteins are also considered part of the invention.

BRIEF DESCRIPTION OF THE DRAWINGS

FIG. 1 provides a graphic representation of the reduction of total saturated fatty acids (C6:0 to C24:0) in pooled seed of Brassica plants containing the Cpu KASI/CpuKASIV and safflower delta-9 desaturase.

FIG. 2 provides a table of fatty acid analysis of oil from soybean transformed with the construct pCGN9807.

DETAILED DESCRIPTION OF THE INVENTION

Figure 3:
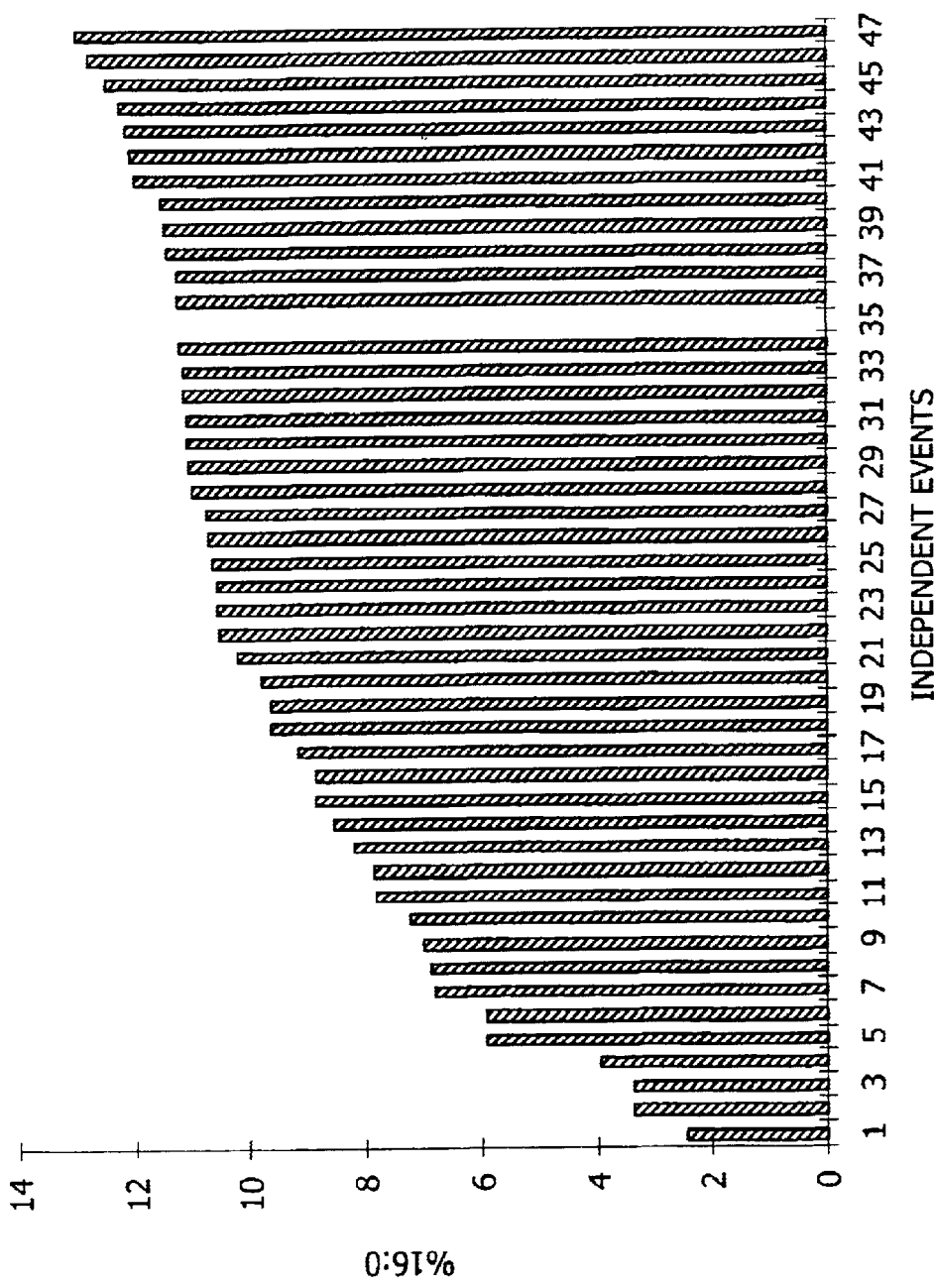
FIG. 3 provides a graphic representation of the C16:0 fatty acid levels in soybean oil from plants containing the expression construct pCGN9807.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, databases, patents, patent applications and other references cited in this application are herein incorporated by reference in their entirety as if each individual publication, patent, patent application or other reference were specifically and individually indicated to be incorporated by reference.

In accordance with the subject invention, isolated nucleotide sequences are provided which are capable of encoding sequences of amino acids, such as, a protein, polypeptide or peptide, which encode β-ketoacyl-ACP synthase (also referred to herein as KAS). The novel nucleic acid sequences find use in the preparation of constructs to direct their expression in a host cell. Furthermore, the novel nucleic acid sequences find use in the preparation of plant expression constructs to modify the saturated fatty acid composition of a host cell. Also provided are plant oil compositions comprising a low level of saturated fatty acids.

Isolated Proteins, Polypeptides and Polynucleotides

A first aspect of the present invention relates to isolated β-ketoacyl-ACP synthase polynucleotides. The polynucleotide sequences of the present invention include isolated polynucleotides that encode the polypeptides of the invention having a deduced amino acid sequence set forth in SEQ ID NO: 2 and to other polynucleotide sequences closely related to such sequences and variants thereof.

The invention provides a polynucleotide sequence identical over its entire length to each coding sequence as set forth in SEQ ID NO: 1. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or pre-pro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequences that encode additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

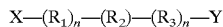

$$X-(R_1)_n-(R_2)-(R_3)_n-Y$$

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence as set forth in SEQ ID NO: 1. In the formula, $R_2$ is oriented so that its 5' end residue is at the left, bound to $R_1$, and its 3' end residue is at the right, bound to $R_3$. Any stretch of nucleic acid residues denoted by any R group, $R_1$, $R_2$ or $R_3$, and where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Nucleotide sequences encoding β-ketoacyl-ACP synthase may be obtained from natural sources or be partially or wholly artificially synthesized. They may directly correspond to a KAS endogenous nucleotide sequence or contain modified amino acid sequences, such as sequences which have been mutated, truncated, increased or the like. β-ketoacyl-ACP synthase may be obtained by a variety of methods, including but not limited to, partial or homogenous purification of protein extracts, protein modeling, nucleic acid probes, antibody preparations and sequence comparisons. Typically a KAS will be derived in whole or in part from a natural source. A natural source includes, but is not limited to, prokaryotic and eukaryotic sources, including, bacteria, yeasts, plants, including algae, and the like.

Of special interest are β-ketoacyl-ACP synthases which are obtainable from cyanobacterial sources, including those which are obtained, from Synechocystis, or from additional sources which are obtainable through the use of these sequences. "Obtainable" refers to those KAS's which have sufficiently similar sequences to that of the sequences provided herein to provide a biologically active protein of the present invention.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotide set forth in SEQ ID NO: 1.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, Cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set forth in SEQ ID NO: 1 under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate CDNA or genomic clones of other genes that have a high sequence similarity to the polynucleotide set forth in SEQ ID NO: 1. Such probes will generally comprise at least about 15 bases. Preferably such probes will have at least about 30 bases and can have at least about 50 bases. Particularly preferred probes will have between about 30 bases and about 50 bases, inclusive.

The coding region of each gene that comprises or is comprised by the polynucleotide sequence set forth in SEQ ID NO: 1 may be isolated by screening using the DNA sequence provided in SEQ ID NO: 1 to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond tothe N-terminal sequence of the polypeptide. The partial sequences so prepared can then be used as probes to obtain KAS clones from a gene library prepared from a cell source of interest. Alternatively, where oligonucleotides of low degeneracy can be prepared from particular peptides, such probes may be used directly to screen gene libraries for gene sequences. In particular, screening of cDNA libraries in phage vectors is useful in such methods due to lower levels of background hybridization.

Typically, a sequence obtainable from the use of nucleic acid probes will show about 60–70% sequence identity between the target KAS sequence and the encoding sequence used as a probe. However, lengthy sequences with as little as about 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have about 20–50% deviation (i.e., about a 50–80% sequence homology) from the sequences used as probe. Oligonucleotide probes can be considerably shorter than the entire nucleic acid sequence encoding a KAS enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related genes. Shorter probes are often particularly useful for polymerase chain reactions (PCR), especially when highly conserved sequences can be identified. (See, Gould, et al., *PNAS USA* (1989) 86:1934–1938).

The skilled artisan will appreciate that, in many cases, an isolated cDNA sequence will be incomplete, in that the region coding for the polypeptide is truncated with respect to the 5' terminus of the cDNA. This is a consequence of the reverse transcriptase, an enzyme with low 'processivity' (a measure of the ability of the enzyme to remain attached to the template during the polymerization reaction) employed during the first strand cDNA synthesis.

There are several methods available and are well know to the skilled artisan to obtain full-length cDNAs, or extend short cDNAs; for example those based on the method of Rapid Amplification of cDNA Ends (RACE) (see, for example, Frohman et al. (1988) *Proc. Natl. Acad. Sci. USA* 85:8998–9002). Recent modifications of the technique, exemplified by the Marathonä technology (Clonetech Laboratories, Inc.) for example, have significantly simplified obtaining full-length cDNA sequences.

Another aspect of the present invention relates to isolated β-ketoacyl-ACP synthase polypeptides. Such polypeptides include the isolated polypeptide set forth in SEQ ID NO: 2, as well as polypeptides and fragments thereof, particularly those polypeptides which exhibit KAS activity and also those polypeptides which have at least about 50%, 60% or 70% identity, preferably at least about 80% identity, more preferably at least about 90% identity, and most preferably at least about 95% identity to the polypeptide sequence set forth in SEQ ID NO: 2, and also include portions of such polypeptides, wherein such portion of the polypeptide preferably includes at least about 30 amino acids and more preferably includes at least about 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine identity.

Parameters for polypeptide sequence comparison typically include the following:
Algorithm: Needleman and Wunsch, *J. Mol. Biol.* 48:443–453 (1970)
Comparison matrix: BLOSSUM62 from Hentikoff and Hentikoff, *Proc. Natl. Acad. Sci USA* 89:10915–10919 (1992)
Gap Penalty: 12
Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:
Algorithm: Needleman and Wunsch, J. Mol. Biol. 48:443–453 (1970)
Comparison matrix: matches=+10; mismatches=0
Gap Penalty: 50
Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

$$X-(R_1)_n-(R_2)-(R_3)_n-Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly the amino acid sequence of SEQ ID NO: 2. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising the polypeptide sequence of SEQ ID NO: 2.

Polypeptides of the present invention have been shown to have β-ketoacyl-ACP synthase activity and are of interest because KAS is involved in the elongation of acetyl-CoA through a condensation reaction with a 2-carbon unit from malonyl-ACP to form β-ketoacyl-ACP. The KAS proteins encoded by the nucleic acid sequences of the present invention demonstrate the ability to elongate various acyl chain lengths by two carbon atoms. Thus the proteins of the present invention are useful in carrying out the condensation of saturated $C_2$–$C_{14}$ and unsaturated $C_{16:1}$–$C_{18:1}$ acyl-ACPs with a $C_2$ unit derived from malonyl-ACP. Furthermore, the protein of the instant invention is useful in carrying out the final elongation of palmitoyl-ACP ($C_{16:0}$) to stearoyl-ACP ($C_{18:0}$).

Fatty acid biosynthesis in higher plants is catalyzed by a set of enzymes located in plastids. Once malonyl-CoA is produced by acetyl-CoA carboxylase (ACCase), the fatty acid synthase (FAS) transfers the malonyl moiety to ACP to use it as a carbon source for the synthesis of long chain fatty acids, mainly 16:0 and 18:0. Each cycle of $C_2$ addition is initiated by a reaction catalyzed by a β-ketoacyl-ACP synthase (KAS) and involves the condensation of a malonyl-ACP with an acyl acceptor. The discovery and subsequent studies of KAS III resulted in significant changes in the understanding of the initial reaction of the fatty acid biosynthesis in plants. The in vitro (Jaworski et al., 1989; Clough et al., 1992) and in vivo (Jaworski et al., 1993) studies established that KAS III initiates the fatty acid synthesis in plants, by catalyzing the condensing reaction of acetyl-CoA and malonyl ACP. Subsequent condensation reactions are catalyzed by other members of KAS family, namely KAS I, II and IV (Shimakata and Stumpf, 1982; Kauppinen et al., 1988; Dehesh et al., 1998)

The polypeptides of the present invention can be mature proteins or can be part of a fusion protein. Fusion proteins can be useful in overcoming certain difficulties that are associated with expression of foreign proteins in the host cells. For example, if the desired protein is degraded or produced in low quantities in the host, it can be fused to a carrier (either a peptide or a protein) that is stable in the host and produced in large quantities or simply produced in large quantities. In this way, an improved stability and higher expression of the desired protein can be achieved. The production of fusion proteins utilizes recombinant DNA techniques previously described in the art and known to a skilled artisan.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that are antigenic or immunogenic in an animal, particularly a human.

Variants of the polypeptide also include polypeptides that vary from the sequence set forth in SEQ ID NO: 2 by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of various host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called pro-proteins.

The polynucleotide and polypeptide sequences can also be used to identify additional sequences which are homologous to the sequences of the present invention. The most preferable and convenient method is to store the sequence in a computer readable medium, for example, floppy disk, CD ROM, hard disk drives, external disk drives and DVD, and then to use the stored sequence to search a sequence database with well known searching tools. Examples of public databases include the DNA Database of Japan (DDBJ) (http://www.ddbj.nig.ac.jp/); Genebank (http://www.ncbi.nlm.nih.gov/web/Genbank/Index.htlm); and the European Molecular Biology Laboratory Nucleic Acid Sequence Database (EMBL) (http://www.ebi.ac.uk/ebi docs/embl db.html). A number of different search algorithms are available to the skilled artisan, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). Additional programs are available in the art for the analysis of identified sequences, such as sequence alignment programs, programs for the identification of more distantly related sequences, and the like, and are well known to the skilled artisan.

Plant Constructs and Methods of Use

Of interest in the present invention, is the use of the nucleotide sequences, or polynucleotides, in recombinant DNA constructs to direct the transcription or transcription and translation (expression) of the β-ketoacyl-ACP synthase sequences of the present invention in a host cell.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

Of particular interest is the use of the nucleotide sequences, or polynucleotides, in recombinant DNA constructs to direct the transcription or transcription and translation (expression) of the KAS sequences of the present invention in a host plant cell. The expression constructs generally comprise a promoter functional in a host cell operably linked to a nucleic acid sequence encoding a KAS of the present invention and a transcriptional termination region functional in a host cell.

By "host cell" is meant a cell which contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. Preferably, host cells are monocotyledenous or dicotyledenous plant cells.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378,619). In addition, it may also be preferred to bring about expression of the protein of interest in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean a' subunit of b-conglycinin (soy 7s, (Chen et al., *Proc. Natl. Acad. Sci.*, 83:8560–8564 (1986))) and oleosin.

It may be advantageous to direct the localization of proteins conferring KAS to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Additional transit peptides for the translocation of the protein to the endoplasmic reticulum (ER) (Chrispeels, K., (1991) *Ann. Rev. Plant Phys. Plant Mol. Biol.* 42:21–53), nuclear localization signals (Raikhel, N. (1992) *Plant Phys.* 100:1627–1632), or vacuole may also find use in the constructs of the present invention.

Depending upon the intended use, the constructs may contain the nucleic acid sequence which encodes the entire KAS protein, or a portion thereof. For example, where antisense inhibition of a given KAS protein is desired, the entire KAS sequence is not required. Furthermore, where KAS sequences used in constructs are intended for use as probes, it may be advantageous to prepare constructs containing only a particular portion of a KAS encoding sequence, for example a sequence which is discovered to encode a highly conserved KAS region.

The skilled artisan will recognize that there are various methods for the inhibition of expression of endogenous sequences in a host cell. Such methods include, but are not limited to antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the β-ketoacyl-ACP synthase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the KAS sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a KAS nucleic acid sequence.

The term "introducing," in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

Plant expression or transcription constructs having a β-ketoacyl-ACP synthase as the DNA sequence of interest for increased or decreased expression thereof may be employed with a wide variety of plant life, particularly, plant life involved in the production of oils for edible and industrial uses. Importantly, the plant expression and/or transcription constructs of the present invention find use in both monocotyledenous and dicotyledenous species, and will be readily applicable to new and/or improved transformation and regulation techniques. Preferred plants include Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, safflower, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

As used herein, the term "plant" includes reference to whole plants, plant organs (for example, leaves, stems, roots, etc.), seeds, and plant cells and progeny of same. Plant cell, as used herein includes, without limitation, seeds suspension cultures, embryos, meristematic regions, callus tissue, leaves roots shoots, gametophytes, sporophytes, pollen, and microspores. The class of plants which can be used in the methods of the present invention is generally as broad as the class of higher plants amenable to transformation techniques, including both monocotyledenous and dicotyledenous plants. Particularly preferred plants include Brassica, soybean, and corn.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

Thus a plant having within its cells a heterologous polynucleotide is referred to herein as a transgenic plant. The heterologous polynucleotide can be either stably integrated into the genome, or can be extra-chromosomal. Preferably, the polynucleotide of the present invention is stably integrated into the genome such that the polynucleotide is passed on to successive generations. The polynucleotide is integrated into the genome alone or as part of a recombinant expression cassette. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

As used herein, a "recombinant expression cassette" is a nucleic acid construct, generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Of interest in the present invention, is the use of expression constructs in plants to produce a reduced level of saturated fatty acids in the plant seed oil.

It is contemplated that the gene sequences may be synthesized, either completely or in part, especially where it is desirable to provide plant-preferred sequences. Thus, all or a portion of the desired structural gene (that portion of the gene which encodes the KAS protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" KAS from a variety of plant sources. Homologous sequences are found when there is an identity of sequence, which may be determined upon comparison of sequence information, nucleic acid or amino acid, or through hybridization reactions between a known KAS and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., *OF URFS and ORFS* (University Science Books, CA, 1986.)

Thus, other β-ketoacyl-ACP synthase can be obtained from the specific exemplified sequences provided herein. Furthermore, it will be apparent that one can obtain natural and synthetic KAS, including modified amino acid sequences and starting materials for synthetic-protein modeling from the exemplified KAS and from KAS which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

For immunological screening, antibodies to the KAS protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the KAS protein. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

The nucleic acid sequences associated with the KAS proteins of the present invention will find many uses. For example, recombinant constructs can be prepared which can be used as probes, or which will provide for expression of the KAS protein in host cells to produce a ready source of the enzyme and/or to modify the composition of fatty acids found therein. Other useful applications may be found when the host cell is a plant host cell, either in vitro or in vivo.

The modification of fatty acid compositions may also affect the fluidity of plant membranes. Different lipid concentrations have been observed in cold-hardened plants, for example. By this invention, one may be capable of introducing traits which will lend to chill tolerance. Constitutive or temperature inducible transcription initiation regulatory control regions may have special applications for such uses.

As discussed above, the nucleic acid sequence encoding a KAS of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired KAS nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a KAS of this invention may be combined with other non-native, or "heterologous", sequences in a variety of ways. By "heterologous" sequences is meant any sequence which is not naturally found joined to the KAS, including, for example, combinations of nucleic acid sequences from the same plant which are not naturally found joined together.

The DNA sequence encoding a KAS of this invention may be employed in conjunction with all or part of the gene sequences normally associated with the KAS. In its component parts, a DNA sequence encoding KAS is combined in a DNA construct having, in the 5' to 3' direction of transcription, a transcription initiation control region capable of promoting transcription and translation in a host cell, the DNA sequence encoding KAS and a transcription and translation termination region.

Potential host cells include both prokaryotic cells, such as *E. coli* and eukaryotic cells such as yeast, insect, amphibian, or mammalian cells. A host cell may be unicellular or found in a multicellular differentiated or undifferentiated organism depending upon the intended use. Preferably, host cells of the present invention include plant cells, both monocotyledenous and dicotyledenous. Cells of this invention may be distinguished by having a KAS foreign to the wild-type cell present therein, for example, by having a recombinant nucleic acid construct encoding a said foreign KAS therein.

The methods used for the transformation of the host plant cell are not critical to the present invention. The transformation of the plant is preferably nonreversible, i.e. by integration of the introduced expression constructs into the host plant genome, so that the introduced constructs are passed onto successive plant generations. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, Agrobacterium infection, liposomes or microprojectile transformation. The skilled artisan can refer to the literature for details and select suitable techniques for use in the methods of the present invention.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli,* and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a nucleic acid sequence of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the first expression construct, or alternatively, transformed plants, one having the first construct and one having the second construct, can be crossed to bring the constructs together in the same plant.

The present invention also provides methods for the production of a plant having a seed oil comprising less than about 5%, preferably less than about 4%, more preferably less than about 3.4% saturated fatty acids as a percentage of the total fatty acids contained in the seed oil. Thus, ranges in the levels of saturated fatty acids in a seed oil range from about 0.5% to about 5% saturated fatty acids as a percentage of total fatty acids, preferably from about 0.5% to about 4% saturated fatty acids.

The methods for the production of a plant having the reduced levels of saturated fatty acids comprise the expression of one or more introduced nucleic acid sequences encoding β-ketoacyl-ACP synthase in a host plant cell. For a greater reduction in the levels of saturated fatty acids, the expression of additional nucleic acid sequences encoding proteins involved in the synthesis of fatty acids can be employed. Such sequences include, but are not limited to: desaturase encoding sequences, including delta 9, delta 12 and delta 15 desaturases, and thioesterase sequences.

The invention now being generally described, it will be more readily understood by reference to the following examples which are included for purposes of illustration only and are not intended to limit the present invention.

EXAMPLES

Example 1

Identification and Characterization of a β-Ketoacyl-ACP Synthase from Synechocystis The genome sequence of the unicellular cyanobacterium, Synechocystis sp. (strain PCC6803) (Kaneko, et a. (1996) *DNA Res.* 3(3):109–136; Kaneko, et al. (1996) *DNA Res.* 3(3):185–209; and Nakamura, et al. (1998) *Nucleic Acids Res.* 26(1):63–67) was searched with the *E. coli* FabF sequence (Magnuson, et al. (1995) *J Bacteriol.* 177(12); 3593–3595) encoding a β-Ketoacyi-ACP Synthase II (KASII) protein. The search identified two sequences in the Synechocystis database (Nakamura, et al. (1998) supra). These sequences were used to design synthetic oligonucleotides for use as primers in Polymerase Chain Reactions (PCR) to isolate the sequence most similar to the KASII class of proteins. The primers 5'-G G A T C C G C A T G C A T G G C A A A T T T G G AAAAGAAACGTGTTGTTGTA-3' (Synch FabF-F, SEQ ID NO: 3) and 5'-GGATCCAAGCTTCTA TTGATATTTTTTGAAAGCTAAGG-3' (Synch FabF-R, SEQ ID NO: 4) were used in PCR reactions with complementary DNA (CDNA) obtained from Synechocystis sp (strain PCC6803). A single reaction product of approximately 1.25 kb was digested with SphI and HindIII and cloned into the respective sites of pQE30 (Invitrogen, Carlsbad, Calif.) to create the construct pCGN8386 for expression in *E. coli*. The sequence was confirmed by sequencing on an automated sequencer, and is provided in SEQ ID NO: 1. The deduced amino acid sequence of the Synechocystis KAS is provided in SEQ ID NO: 2.

The *E. coli* expression vector pCGN8386 is transformed into *E. coli*, and recombinant protein is affinity purified and analyzed for enzyme activity using methods described by Edwards, et al. (1997) *FEBS Letters* 402:62–66. The results of the enzyme assay are provided in Table 1 below.

TABLE 1

|  | 12:0 | 16:0 | 16:1 | 16:0/16:1 |
| --- | --- | --- | --- | --- |
| *E coli* FabB | 1.00 | 0.02 | 0.03 | 0.67 |
| Syn FabF | 1.00 | 0.15 | 0.30 | 0.48 |
| *E coli* FabF | 1.00 | 0.03 | 0.30 | 0.02 |

Results of the enzyme activity assay indicate that except for a higher activity on 16:0-ACP substrates, the Synechocystis KAS has a profile identical to that of the FabF enzyme of *E. coli*.

Example 2

Complementation of *E coli* FabF Mutants

The Synechocystis FabF sequence was analyzed for complementation of the mutant *E coli* FabF (Garwin, et al. (1980) *J Biol Chem* 255(8):3263–3265). Expression of the Syn FabF did not complement the FabF mutation in *E. coli*.

Comparisons of the Syn FabF crystal structure and the *E. coli* FabF structure (Moche, et al. (2000) *J. Mol. Biol.*) shows that the major difference between the two is the substitution of glycine (G) at position 202 to serine (S) and phenylalanine (F) at position 137 to methionine (M) in the Syn FabF.

To investigate the role of these mutations in the Syn FabF, mutations were introduced into the Syn FabF sequence that convert S202 to G and M137 to F. Expression of these two mutated Syn FabF sequences were able to complement the *E. coli* mutant.

Example 3

Plant Expression Construct Preparation

A series of expression constructs are prepared for transformation into various plants, either alone, or in combination with additional sequences encoding proteins involved in fatty acid biosynthesis.

The construct pCGN8378 is a double napin expression cassette for the seed preferential expression of the *Cuphea pullcherrima* KASI (cpuKAS B/7-8, described in PCT Publication WO 98/46776, the entirety of which is incorporated herein by reference) and KASIV (cpuKAS A/p7-6A, described in PCT Publication WO 98/46776, the entirety of which is incorporated herein by reference) sequences in Brassica.

In addition, a double expression cassette construct, pCGN9807, was prepared to express the *C. Pullcherrimma* KASI and KASIV sequences from promoters derived from the soybean a' subunit of b-conglycinin (soy 7s, (Chen et al., (1986), *Proc. Natl. Acad. Sci.,* 83:8560–8564)) for transformation into soybean cells. The pCGN9807 construct provides for the seed preferential expression of the KAS sequences in the soybean seed cells.

The plant expression construct, pCGN3231, for the expression of the safflower Delta-9 desaturase from the napin promoter sequence is as described in U.S. Pat. No. 5,723,595, the entirety of which is incorporated herein by reference.

Another construct, the safflower Delta-9 desaturase expression construct, is also prepared for the seed preferential expression of the sequence from the 7S promoter. This construct, pCGN9373, contains the safflower delta-9 desaturase coding sequence under the control of the soy 7S promoter and the pea rbcS termination sequences.

For expression of the Syn FabF sequence in soybean, a construct was prepared to express the FabF sequence in combination with a delta-9 desaturase sequence from safflower (G. Thompson, et al., Primary structure of the precursor and mature forms of stearoyl-acyl carrier protein desaturase from safflower embryos and requirement of ferredoxin for enzyme activity, *Proc. Natl. Acad. Sci. USA,* Vol 88, pp 2578–2582, March 1991). The construct was prepared by first PCR amplifying a transit peptide from *Cuphea hookeriana* KASII-7 (described in PCT Publication WO 98/46776) using the primers KASII-7 tpF 5'-CTGAGATCTGTCGACATGGCGACCGCTT CTCGC-3' (SEQ ID NO: 5) and KASII-7 tpR 5'-GACAGATCTTGTGGAGACTTCCTGTGCAGG-3' (SEQ ID NO: 6). The resulting fragment was digested with BglII and placed 5' (upstream) of the Syn FabF cDNA by cloning into the BamHI site of pCGN8386 to create pCGN9382. A SalI/HindIII fillin fragment from pCGN9382 containing the Ch KASII-7/Syn FabF was cloned into the XhoI/EcoRI fillin pCGN3892 between the 7S promoter and pea rbcS terminator to generate pCGN9868.

A second construct for the expression of the delta-9 desaturase sequence was also prepared. The safflower delta-9 desaturase was digested from pCGN3231 (described in U.S. Pat. No. 5,723,595, the entirety of which is incorporated herein by reference) as a XhoI fragment into the same site of pCGN3892 7S expression cassette to create pCGN9359. A NotI fragment containing the delta-9 desaturase expression cassette from pCGN9359 was ligated into the NotI site of pMON33510 to generate the vector pCGN9882. The plant transformation construct pCGN9883 was created by ligating a SalI/SwaI fragment containing the Syn FabF transit peptide fusion from pCGN9868 into the SnsBI/SalI of pCGN9882.

Example 4

Complementation of Arabidopsis FabF Mutants

Expression of the Syn FabF coding sequence in a Fab1 mutant line of Arabidopsis (Wu, et al. (1997) *Plant Physiol.* 113(2):347–356) complemented the phenotype. Mutant lines expressing the Syn FabF demonstrate a level of 16:0 reduced from the 16% of the mutant to similar to wildtype Arabidopsis (8%). Thus, the Synechocystis KAS sequence is able to complement the Arabidopsis fab1 mutant phenotype.

Example 5

Transgenic Plant Analysis

5A. Transgenic Brassica Oils Analysis

Transgenic Brassica plants containing the plant expression construct pCGN3231 were crossed with transgenic Brassica plants containing the expression construct pCGN8378. Fatty acid compositional analysis was performed using gas chromatography of fatty acid methyl esters (FAME) derived from seed oil obtained from transgenic Brassica lines. Results of the analysis are provided in Table 2 as well as in FIG. 1. The total saturates column is the total of the C6:0, C8:0, C10:0, C12:0, C14:0, C16:0, C18:0, C20:0, C22:0 and C24:0 fatty acids found in the oil.

TABLE 2

| Plant Line | C16:0 | C18:0 | C20:0 | C20:1 | Total Saturates |
|---|---|---|---|---|---|
| DH37-4 | 1.74 | 1.00 | 0.30 | 3.84 | 3.19 |
| DH37-5 | 1.62 | 1.04 | 0.30 | 4.22 | 3.10 |
| DH95-1 | 1.76 | 0.83 | 0.34 | 6.27 | 3.17 |
| DH95-2 | 1.69 | 0.88 | 0.38 | 6.68 | 3.21 |
| DH95-6 | 1.65 | 0.86 | 0.38 | 6.75 | 3.13 |
| DH97-2 | 1.89 | 0.94 | 0.27 | 3.21 | 3.20 |
| DH97-3 | 1.90 | 0.96 | 0.28 | 3.23 | 3.29 |
| DH135-2 | 1.66 | 1.19 | 0.33 | 6.93 | 3.35 |
| DH135-4 | 1.60 | 1.10 | 0.30 | 6.57 | 3.12 |
| DH199-2 | 1.56 | 0.96 | 0.29 | 6.83 | 3.04 |
| DH199-4 | 1.60 | 0.96 | 0.29 | 6.39 | 3.12 |
| DH229-1 | 1.69 | 1.01 | 0.30 | 5.62 | 3.16 |
| DH240-2 | 1.90 | 0.84 | 0.33 | 5.81 | 3.38 |
| DH240-4 | 1.70 | 0.88 | 0.33 | 5.95 | 3.21 |
| DH266-6 | 1.82 | 0.83 | 0.34 | 5.67 | 3.31 |
| DH561-1 | 1.75 | 0.98 | 0.40 | 7.30 | 3.35 |
| DH561-6 | 1.81 | 0.92 | 0.39 | 5.01 | 3.35 |
| DH591-2 | 1.70 | 0.91 | 0.37 | 5.15 | 3.29 |
| DH591-6 | 1.71 | 0.90 | 0.39 | 5.16 | 3.34 |

Total level of saturated fatty acids in oil obtained from seed containing the *Cuphea pulicherima* KASI and KASIV sequences as well as the safflower delta-9 desaturase demonstrate a significantly decreased amount of total saturates as compared to non-transformed control Brassica lines. Levels of total saturated fatty acids are reduced to about 3.0 wt %, and below 3.4 wt %, while the levels of total saturated fatty acids obtained in non-transformed controls lines are about 6.0 wt %.

5B. Transgenic Soybean Oils Analysis

Figure 4:
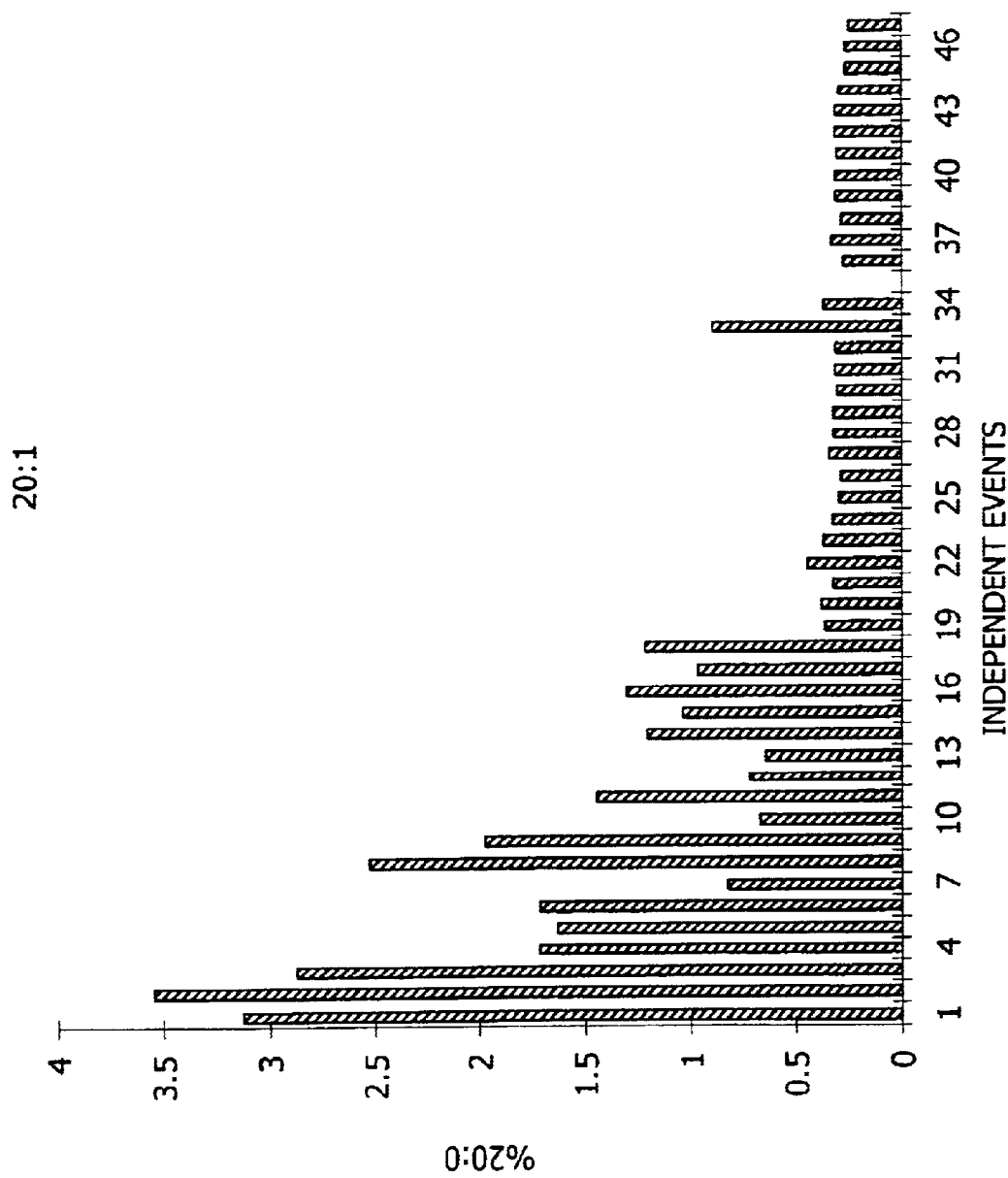
FIG. 4 provides a graphic representation of the C20:1 fatty acid levels in soybean oil from plants containing the expression construct pCGN9807.

Seed oil obtained from transgenic soybean plants containing the construct pCGN9807 are analyzed for fatty acid composition using gas chromatography of fatty acid methyl esters. The results show that the transgenic 9807 lines demonstrate a reduced amount of total saturated fatty acids compared to non-transgenic wild-type (FIG. 2). In particular, levels of C16:0 fatty acids are reduced to less than 2.5 wt %, compared to normal levels of about 13 wt % (FIG. 3). In addition, the levels of C20:1 are also increased in the seed oils of transgenic plants containing the KASI and KASIV sequences (FIG. 4).

Transgenic soybean plants containing the expression construct pCGN9883 were analyzed for fatty acid composition using gas chromatography of fatty acid methyl esters (FAME) derived from oils obtained from various lines. Oil analyses data from T2 segregation generation of soybean seed showed that the levels of 16:0 has dropped from between about 13 and about 16% in non-transgenic control lines to about 2.1% in the seed oils of transgenic soybean plants. These levels are as low as those obtained with the combined expression of KASI(B) and KASIV(A) enzyme shown above. Thus, expression of the Synechocystis fabF alone can decrease the levels of saturated fat in a host plant cell and can be combined with delta 9 desaturase to further reduce the amount of saturated fatty acids in a host cell. To bring the levels of saturated fat to $\leq 3.2$ wt % as defined by FDA, one may need to include the strategy of silencing FatB thioestearse from soy by sense and/or anti-sensing the introns, negative dominant mutations, and targeting the FatB promoter to interfere with the expression of this gene.

The above results demonstrate that the Synechocystis FabF sequence can be used in the preparation of constructs for expression in host cells. Furthermore, expression of the KAS sequences, either alone or in combination with additional sequences encoding proteins involved in fatty acid biosynthesis can be used in the preparation of transgenic plants having reduced saturated fatty acid content.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. An isolated polynucleotide selected from the group consisting of:
   a) A nucleotide sequence comprising SEQ ID NO: 1; and
   b) A nucleotide sequence complementary to the nucleotide sequence of (a).

2. The isolated polynucleotide of claim 1 comprising SEQ ID NO:1.

3. A nucleic acid construct comprising a promoter functional in a host cell operably linked to the polynucleotide of claim 1.

4. The nucleic acid construct according to claim 3, wherein said polynucleotide is operably linked in an orientation relative to said promoter selected from the group consisting of sense and antisense.

5. The nucleic acid construct according to claim 4, wherein said polynucleotide is operably linked to a construct encoding for a desaturase enzyme.

6. The nucleic acid construct according to claim 5, wherein said construct encoding for a desaturase enzyme encodes for a delta-9 desaturase enzyme.

7. A host cell modified by introducing the nucleic acid construct of claim 3.

8. The host cell of claim 7, wherein said host cell is a plant host cell.

9. A transgenic plant, or any part thereof, comprising the host cell of claim 8.

10. The transgenic plant, or any transgenic part thereof, of claim 9, wherein said transgenic plant is selected from the group consisting of Brassica, soybean, and corn.

11. A transgenic seed from the transgenic plant of claim 9.

12. A transgenic progeny from the transgenic plant of claim 9.

13. A transgenic seed from the progeny of claim 12.

14. A transgenic plant, or any part thereof, from the seed of claim 11.

15. The plant according to claim 10, wherein said plant is a soybean plant.

16. The plant according to claim 15, wherein a seed from said plant contains less than about 3.5% weight percent saturated fatty acid.

17. The plant according to claim 10, wherein said plant is a corn plant.

18. The plant according to claim 17, wherein a seed from said plant contains less than about 3.5% weight percent saturated fatty acid.

19. The plant according to claim 10, wherein said plant is a Brassica plant.

20. The plant according to claim 19, wherein a seed from said plant contains less than about 3.5% weight percent saturated fatty acid.

* * * * *

SEQUENCE LISTING

<160> NUMBER OF SEQ ID NOS: 6

<210> SEQ ID NO 1
<211> LENGTH: 1275
<212> TYPE: DNA
<213> ORGANISM: Synechocystis sp.

-continued

```
<400> SEQUENCE: 1
ggatccgcat gcatggcaaa tttggaaaag aaacgtgttg ttgtaacggg attgggagcc      60
atcaccccca tcggtaatac tctccaagac tattggcaag cttaatggag ggtcgtaac     120
ggcattggcc ccattacccg tttcgatgct agtgaccaag cctgccgttt tggaggggaa     180
gtaaaggatt tgatgctac ccagtttctt gaccgcaaag aagctaaacg gatggaccgg      240
ttttgccatt tgctgtttg tgccagtcaa caggcaatta cgatgctaag ttggtgatt      300
aacgaactca atgccgatga atcgggggta ttgattggca cgggcattgg tggtttgaaa     360
gtactggaag atcaacaaac cattctgttg ataagggtc ctagccgttg cagtcctttt      420
atgatcccga tgatgatcgc caacatggcc tctgggttaa ccgccatcaa cttaggggcc     480
aagggtccca ataactgtac ggtgacggcc tgtgcggcgg ttccaatgc cattggagat      540
gcgtttcgtt tggtgcaaaa tggctatgct aaggcaatga tttgcggtgg cacggaagcg     600
gccattaccc cgctgagcta tgcaggtttt gcttcggccc gggctttatc tttccgcaat     660
gatgatcccc tccatgccag tcgtccctttc gataaggacc gggatggttt tgtgatgggg     720
gaaggatcgg gcattttgat cctagaagaa ttggaatccg ccttggcccg gggagcaaaa     780
atttatgggg aaatggtggg ctatgccatg acctgtgatg cctatcacat taccgcccca     840
gtgccggatg gtcggggagc caccagggcg atcgcctggg ccttaaaaga cagcggattg     900
aaaccggaaa tggtcagtta catcaatgcc catggtacca gcaccctgc taacgatgtg     960
acggaaaccc gtgccattaa acaggcgttg gaaatcatg cctacaatat tgcggttagt    1020
tctactaagt ctatgaccgg tcacttgttg ggcggctccg gaggtatcga agcggtggcc    1080
accgtaatgg cgatcgccga agataaggta cccccccacca ttaatttgga gaaccccgac    1140
cctgagtgtg atttggatta tgtgccgggg cagagtcggg ctttaatagt ggatgtagcc    1200
ctatccaact ccttttggttt tggtggccat aacgtcacct tagctttcaa aaaatatcaa    1260
tagaagcttg gatcc                                                    1275

<210> SEQ ID NO 2
<211> LENGTH: 416
<212> TYPE: PRT
<213> ORGANISM: Synechocystis sp.

<400> SEQUENCE: 2

Met Ala Asn Leu Glu Lys Lys Arg Val Val Thr Gly Leu Gly Ala
1               5                   10                  15

Ile Thr Pro Ile Gly Asn Thr Leu Gln Asp Tyr Trp Gln Gly Leu Met
            20                  25                  30

Glu Gly Arg Asn Gly Ile Gly Pro Ile Thr Arg Phe Asp Ala Ser Asp
        35                  40                  45

Gln Ala Cys Arg Phe Gly Gly Glu Val Lys Asp Phe Ala Thr Gln
    50                  55                  60

Phe Leu Asp Arg Lys Glu Ala Lys Arg Met Asp Arg Phe Cys His Phe
65                  70                  75                  80

Ala Val Cys Ala Ser Gln Gln Ala Ile Asn Asp Ala Lys Leu Val Ile
                85                  90                  95

Asn Glu Leu Asn Ala Asp Glu Ile Gly Val Leu Ile Gly Thr Gly Ile
            100                 105                 110

Gly Gly Leu Lys Val Leu Glu Asp Gln Gln Thr Ile Leu Leu Asp Lys
        115                 120                 125

Gly Pro Ser Arg Cys Ser Pro Phe Met Ile Pro Met Met Ile Ala Asn
```

```
            130                 135                 140
Met Ala Ser Gly Leu Thr Ala Ile Asn Leu Gly Ala Lys Gly Pro Asn
145                 150                 155                 160

Asn Cys Thr Val Thr Ala Cys Ala Ala Gly Ser Asn Ala Ile Gly Asp
                165                 170                 175

Ala Phe Arg Leu Val Gln Asn Gly Tyr Ala Lys Ala Met Ile Cys Gly
            180                 185                 190

Gly Thr Glu Ala Ala Ile Thr Pro Leu Ser Tyr Ala Gly Phe Ala Ser
        195                 200                 205

Ala Arg Ala Leu Ser Phe Arg Asn Asp Pro Leu His Ala Ser Arg
    210                 215                 220

Pro Phe Asp Lys Asp Arg Asp Gly Phe Val Met Gly Glu Gly Ser Gly
225                 230                 235                 240

Ile Leu Ile Leu Glu Glu Leu Glu Ser Ala Leu Ala Arg Gly Ala Lys
                245                 250                 255

Ile Tyr Gly Glu Met Val Gly Tyr Ala Met Thr Cys Asp Ala Tyr His
            260                 265                 270

Ile Thr Ala Pro Val Pro Asp Gly Arg Gly Ala Thr Arg Ala Ile Ala
        275                 280                 285

Trp Ala Leu Lys Asp Ser Gly Leu Lys Pro Glu Met Val Ser Tyr Ile
    290                 295                 300

Asn Ala His Gly Thr Ser Thr Pro Ala Asn Asp Val Thr Glu Thr Arg
305                 310                 315                 320

Ala Ile Lys Gln Ala Leu Gly Asn His Ala Tyr Asn Ile Ala Val Ser
                325                 330                 335

Ser Thr Lys Ser Met Thr Gly His Leu Leu Gly Ser Gly Gly Ile
            340                 345                 350

Glu Ala Val Ala Thr Val Met Ala Ile Ala Glu Asp Lys Val Pro Pro
        355                 360                 365

Thr Ile Asn Leu Glu Asn Pro Asp Pro Glu Cys Asp Leu Asp Tyr Val
    370                 375                 380

Pro Gly Gln Ser Arg Ala Leu Ile Val Asp Val Ala Leu Ser Asn Ser
385                 390                 395                 400

Phe Gly Phe Gly Gly His Asn Val Thr Leu Ala Phe Lys Lys Tyr Gln
                405                 410                 415

<210> SEQ ID NO 3
<211> LENGTH: 45
<212> TYPE: DNA
<213> ORGANISM: Synechocystis sp.

<400> SEQUENCE: 3
ggatccgcat gcatggcaaa tttggaaaag aaacgtgttg ttgta        45

<210> SEQ ID NO 4
<211> LENGTH: 38
<212> TYPE: DNA
<213> ORGANISM: Synechocystis sp.

<400> SEQUENCE: 4
ggatccaagc ttctattgat attttttgaa agctaagg              38

<210> SEQ ID NO 5
<211> LENGTH: 33
<212> TYPE: DNA
<213> ORGANISM: Cuphea hookeriana
```

```
<400> SEQUENCE: 5
ctgagatctg tcgacatggc gaccgcttct cgc                              33

<210> SEQ ID NO 6
<211> LENGTH: 30
<212> TYPE: DNA
<213> ORGANISM: Cuphea hookeriana

<400> SEQUENCE: 6
gacagatctt gtggagactt cctgtgcagg                                  30
```